United States Patent
Deshpande

(10) Patent No.: US 9,517,324 B2
(45) Date of Patent: Dec. 13, 2016

(54) EXTENDABLE INTRAVENOUS CATHETER

(71) Applicant: The Board of Trustees of the University of Illinois, Urbana, IL (US)

(72) Inventor: Girish G. Deshpande, Peoria, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/210,866

(22) Filed: Mar. 14, 2014

(65) Prior Publication Data

US 2014/0276619 A1  Sep. 18, 2014

Related U.S. Application Data

(60) Provisional application No. 61/791,289, filed on Mar. 15, 2013.

(51) Int. Cl.
*A61M 25/00* (2006.01)
*A61M 25/06* (2006.01)
*A61M 25/01* (2006.01)

(52) U.S. Cl.
CPC ..... *A61M 25/0074* (2013.01); *A61M 25/0021* (2013.01); *A61M 25/0606* (2013.01); *A61M 25/00* (2013.01); *A61M 25/003* (2013.01); *A61M 25/008* (2013.01); *A61M 25/0102* (2013.01); *A61M 25/0152* (2013.01); *A61M 2025/0025* (2013.01); *A61M 2025/0063* (2013.01); *A61M 2025/0175* (2013.01)

(58) Field of Classification Search
CPC ................ A61M 2025/0063; A61M 25/0102; A61M 25/003; A61M 25/9921; A61M 25/008; A61M 25/0152; A61M 39/00; A61M 25/00; A61M 25/0021; A61M 2025/0025

See application file for complete search history.

(56) References Cited

U.S. PATENT DOCUMENTS

| | | | | |
|---|---|---|---|---|
| 4,276,874 A * | 7/1981 | Wolvek et al. | | 600/18 |
| 5,449,343 A * | 9/1995 | Samson et al. | | 604/95.01 |
| 5,643,229 A * | 7/1997 | Sinaiko | | 604/267 |
| 5,674,271 A * | 10/1997 | Denker | | 607/119 |
| 6,669,689 B2 * | 12/2003 | Lehmann | | A61B 18/02 606/22 |
| 7,004,937 B2 * | 2/2006 | Lentz et al. | | 606/22 |
| 2002/0165553 A1 * | 11/2002 | Elbert | | A61B 17/3415 606/108 |
| 2011/0066139 A1 * | 3/2011 | Winegar | | 604/524 |

* cited by examiner

*Primary Examiner* — Imani Hayman
*Assistant Examiner* — Nilay Shah
(74) *Attorney, Agent, or Firm* — McDonnell Boehnen Hulbert & Berghoff LLP

(57) ABSTRACT

An intravenous catheter has a tip portion, an extendable portion and a proximal portion attached to a hub. The extendable portion has a refracted position and an extended position. A wire may be incorporated in the intravenous portion. The wire may have a receiver disposed in the tip portion. An extender tool is insertable and removable from the catheter. The extender is dimensioned to engage the receiver upon insertion into said catheter and lengthen the extendable portion of said catheter to said extended position when inserted.

17 Claims, 2 Drawing Sheets

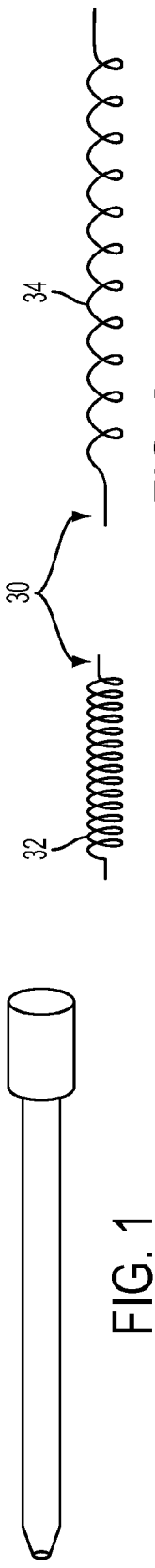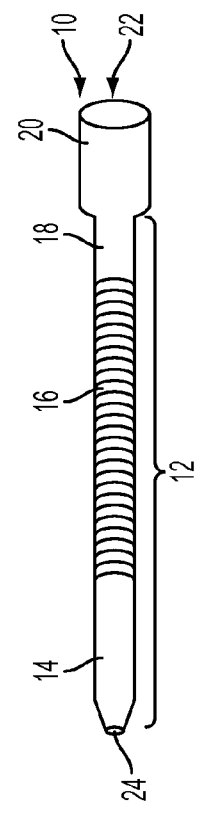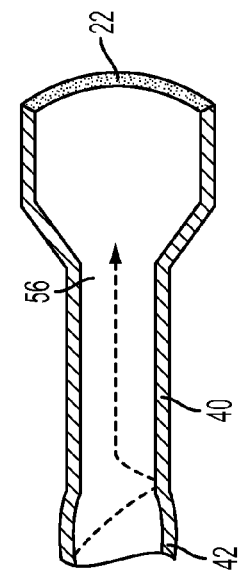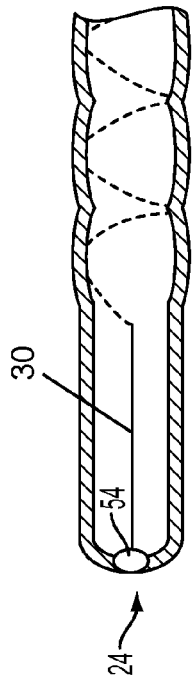

EXTENDABLE INTRAVENOUS CATHETER

CROSS-REFERENCE TO RELATED APPLICATIONS

This application claims the benefit of U.S. Provisional Patent Application No. 61/791,289 filed Mar. 15, 2013, which is hereby incorporated by reference in its entirety.

FIELD OF THE INVENTION

This invention is in the field of intravenous catheters, methods of using the catheters and a kit comprising the catheters.

BACKGROUND

Intravenous catheters are used for administration of intravenous medications, fluids and blood products routinely in emergency departments, hospitals and other patient care areas. Placing a peripheral venous catheter (PIV), is relatively easy in adults, but can be tedious, difficult (even for an experienced provider) and time consuming in infants and younger children as they have smaller and more fragile veins than adults and the veins are difficult to locate and stabilize while inserting and securing the catheter.

Once placed, it is harder to maintain the catheter in place, due to its short length, constant movement of the extremity and non-cooperation from younger children. Under the age of 5 years, the mean duration of patency of catheters is less than two days and it is shorter for infants and neonates. Maintenance of patency of these catheters is important for reducing patient discomfort and need for restarting of the PIV. Fewer IV restarts can reduce pain and anxiety to the patient and its family members; conserve supplies and professional time for any busy hospital.

When IV therapy is needed for a longer duration, peripherally inserted central venous catheters (PICC) are used. These catheters require provider expertise on the part of the provider, ultrasound guidance and special catheter kits and may also require fluoroscopy. PICC line placement, especially in children, is time consuming and can be associated with similar complications as central venous catheters including thrombosis, infection and bleeding. Accordingly there is an ongoing need for a catheter that can be placed by clinical providers without the need special training and will last longer than traditional IV catheters.

SUMMARY

The invention is an extendable intravenous catheter. The catheter is configured as a conventional catheter for purposes of insertion and placement. However, the catheter may be lengthened after placement to extend farther into the vessel.

The catheter includes a hub and an intravenous portion having fluid communication therethrough. The intravenous portion has a tip portion, an extendable portion and a proximal portion attached to the hub. The extendable portion has a retracted position and an extended position. An extender tool is insertable and removable from the catheter. The extender tool is dimensioned for passing through said hub, proximal portion and extendable portion but not through said opening in said tip portion such that said extenable portion may be extended to its extended position by inserting and applying sufficient pressure to said extender tool.

In another embodiment, a wire is incorporated in the intravenous portion. The wire includes a coiled portion that supports maintenance of said intravenous portion of said catheter in said extended position In another embodiment, the wire has a receiver disposed in the tip portion.

In another embodiment, this invention is a method of inserting a catheter into a patient comprising inserting into the patient an extendable catheter of the invention wherein the extendable portion is in its retracted position, inserting the extender tool into said catheter and exerting sufficient pressure on said extender tool to extend the catheter to its full length.

In another embodiment, this invention is a kit comprising an extendable catheter of the invention and an extender tool.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Embodiments of the present invention will become more fully understood from the detailed description and the accompanying drawings, wherein:

FIG. 1 shows a prior art intravenous catheter.

FIG. 2 shows an extendable intravenous catheter of the present invention.

FIG. 3 shows a coiled and unwound spring.

FIG. 4 depicts an embodiment of the extender tool.

FIG. 5 is a cut away side view of an embodiment of the extendable intravenous catheter.

DETAILED DESCRIPTION

Figure 6:
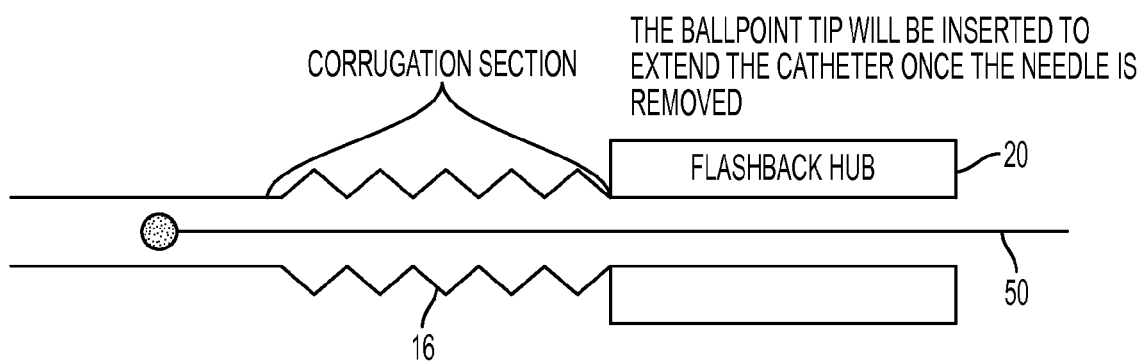
FIG. 6 is a cut away side view of an embodiment of the extendable intravenous catheter with the extender tool inserted.

The following description of the preferred embodiment(s) is merely exemplary in nature and is in no way intended to limit the invention, its application, or uses.

FIG. 1 shows a prior art intravenous catheter without a needle. FIG. 2 shows an extendable intravenous catheter of the present invention 10 without a needle. The extendable intravenous catheter of the present invention 10 includes an intravenous portion 12, which is further comprised of a tip portion 14, an extendable portion 16 and a proximal portion 18. The proximal portion 18 is attached to or integrally formed with a hub 20. An entrance opening 22 in the hub 20 is in fluid communication with an outlet tip, outlet 24 because all of these portions are assembled together or integrally formed to create a continuous lumen from the hub entry to the tip outlet. This patent lumen will accommodate a needle for placement of the IV, followed by an extender to dispose the catheter in the vessel and finally throughput of fluid solutions containing therapeutic agents.

The extendable portion 16 has a first position which is retracted and short relative to a second position, which is extended and long.

In an embodiment, the intravenous portion 12 of the catheter 10 includes a wire 30. Wire 30 has a retracted configuration 32 which is compacted in an axial direction and wound relatively tightly. The wire 30 has no memory for retaining this configuration 32. The wire 30 may be extended to an extended position 34, which is relatively less compacted axially, unwound and long. The metal or other material of which spring 30 is fabricated is selected for retaining the extended configuration 30 after having been placed in the extended configuration 34.

As is seen in the cutaway side view of FIG. 5, in an embodiment of the invention, the entrance opening 22 and tip outlet 24 are in fluid communication through a patent lumen throughout the catheter 10. The side wall 40 of the catheter 10 includes wire 30. Wire 30 may be embedded in the side wall 40, attached to an outer wall or an inner wall of said side wall 40 or sandwiched between laminated layers of said wall 40 as at layer 42 for example. In a preferred embodiment, the interior lumen of the catheter maintains a smooth wall. In an alternate embodiment (not shown), the wire 30 could be completely omitted, as long as the receiver 54 is sturdy enough to withstand axial force generated by the extender tool, and to maintain a lengthened position after being extended in situ.

As can be seen in FIG. 4, an extender tool 50 is provided. In the depicted embodiment, the extender tool 50 comprises a relatively stiff wire that includes a ball end 52. Referring now to FIG. 5, the wire 30 includes a receiver 54. In the depicted embodiment, the receiver 54 is a loop in the end of the wire disposed proximate to the tip outlet 24. The receiver loop 54 is dimensioned to have a diameter smaller than ball 52 at the end of extender 50.

The catheter of the invention can be constructed of any material that is biocompatible and hemocompatible. Suitable biomaterials include polytetrafluorethylene (PTFE), polyvinyl chloride (PVC), and polyurethane (PU). In an embodiment, the catheter will be constructed using PTFE because it has a greater rate of hemocompatibility than PVC or PU, as well as a longer duration period.

In operation, the catheter with the extendable portion 16 in its retracted position has a needle placed therein, with the point of the needle extending through the tip outlet 24. The IV is placed in the conventional manner. Once free flow of blood is obtained indicating the presence of the needle in the lumen of the vein, the needle is withdrawn and through the outlet opening 22, the extender 50 is placed within the catheter 10. Appropriate pressure is placed by the operator on the extender 50 in order to place its ball end 52 against receiver 54 of wire 30 and thereafter extend wire 30 and the intravenous catheter extendable portion 16 to move it from the retracted short position to the extended long position. Thereafter, the extender 50 is withdrawn. The wire 30 maintains its extended configuration 34 and supports the catheter in retaining its long, extended configuration for its in-dwelling duration.

In the depicted embodiment, the wall 40 of the intravenous portion 12 of the catheter includes an accordion shape or corrugated configuration having its outer pleats substantially corresponding to the coiled portion of said wire 30. Thus, the material of side wall 40 can contribute to the provision in the overall catheter of a first short retracted position and then an extended long position during its indwelling use. In the embodiment depicted, the wire 30 has a proximal end anchored substantially within or near said hub 20.

The catheter may be manufactured in various lengths and gauges depending on its intended use. The catheter gauge will be essentially identical to that of conventional, non-extendable catheters used for a given application. Selection and placement of the extendable catheter for a given application is well within the skill of the clinical provider. Typically the catheter will be extendable to about 3 to about 5 times its unextended length. For example, in certain embodiments, the catheter may have an unextended length of up to about 1.5 inches and an extended length of up to about 4.5 to about 7.5 inches within the patient. In other embodiments, the catheter will have a fully extended length between the lengths of a peripheral IV and that of a PICC.

Just after birth, the average upper arm length is 4.1 inches, while at 5 years old the length is 7.5 inches. This particular invention is applicable for all ages but is particularly applicable to the younger age groups. The gauge and length of the catheter will depend on the age and size of the patient as determined by the provider. The catheter material will be biocompatible, and smooth on the outside when extended. Like a PICC, our catheter will be inserted peripherally, but it will require less training for nurses and a shorter insertion time.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

I claim:

1. An intravenous catheter comprising:
    a hub;
    a tip portion comprising an opening;
    a proximal portion attached to the hub; and
    an extendable portion disposed between the proximal portion and the tip portion, the extendable portion having a retracted position and an extended position and comprising a wire incorporated therein and anchored to the hub, the wire comprising a coiled portion,
    wherein the extendable portion is configured to be extended from the retracted position to the extended position by an extender tool and to retain the extended position after removal of the extender tool, the extender tool being insertable and removable from the catheter and dimensioned for passing through the hub, the proximal portion, and the extendable portion but not through the opening in the tip portion.

2. The intravenous catheter according to claim 1, further comprising a receiver disposed in the tip portion, the receiver being configured to reversibly engage the extender tool.

3. The intravenous catheter according to claim 1, wherein the wire supports maintenance of an intravenous portion of the catheter in the extended position.

4. The intravenous catheter according to claim 3, wherein the wire further comprises a receiver disposed in the tip portion, the receiver capable of engaging the extender tool.

5. The intravenous catheter according to claim 4, wherein the extender tool comprises a ball point tip.

6. The intravenous catheter according to claim 3, wherein the wire further comprises a receiver disposed in the tip portion, the receiver comprising a loop having a smaller diameter than a diameter of a ball at an end of the extender tool.

7. The intravenous catheter according to claim 1, wherein the extendable portion comprises a side wall and the wire is attached to the side wall.

8. The intravenous catheter according to claim 7, wherein the wire is embedded in the side wall.

9. The intravenous catheter according to claim 8, wherein the side wall comprises at least one layer and wherein the wire is positioned within the at least one layer.

10. A kit comprising:
an intravenous catheter, comprising:
a hub;
a tip portion comprising an opening;
a proximal portion attached to the hub;
an extendable portion disposed between the proximal portion and the tip portion and comprising a wire incorporated therein and anchored to the hub, the wire comprising a coiled portion and supporting maintenance of an intravenous portion of the catheter in the extended position, the extendable portion having a first position and a second position, wherein the first position is short relative to the second position; and
an extender tool that is removably insertable into the catheter and is dimensioned for passing through the hub, the proximal portion, and the extendable portion but not through the opening,
wherein pressure exerted by the extender tool on a receiver of the catheter transitions the catheter from the first position to the second position and the catheter maintains the second position after subsequent removal of the extender tool from the catheter.

11. The kit according to claim 10, wherein the extendable portion comprises a side wall and the wire is attached to the side wall.

12. The kit according to claim 11, wherein the wire comprises the receiver which is disposed in the tip portion to engage the extender tool.

13. The kit according to claim 12, wherein the extender tool comprises a ball point tip.

14. The kit according to claim 11, wherein the wire is embedded in the side wall.

15. The kit according to claim 11, wherein the side wall comprises at least one layer and wherein the wire is positioned within the at least one layer.

16. The kit according to claim 10, wherein a receiver further comprises a loop comprising a smaller diameter than a diameter of a ball at an end of the extender tool.

17. The kit according to claim 10, wherein the receiver is disposed in the tip portion, the receiver being configured to reversibly engage the extender tool.

\* \* \* \* \*